United States Patent
Kim et al.

(10) Patent No.: US 8,864,597 B2
(45) Date of Patent: Oct. 21, 2014

(54) FEEDBACK APPARATUS AND METHOD FOR IMPROVING WEIGHT SHIFT

(71) Applicant: Korea Institute of Science and Technology, Seoul (KR)

(72) Inventors: Jin Wook Kim, Seoul (KR); An Jin Park, Seoul (KR); Hyeong Rae Choi, Seoul (KR); Sung Kuk Chun, Asan-si (KR); Dong Hoon Kang, Yangsan-si (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 13/684,334

(22) Filed: Nov. 23, 2012

(65) Prior Publication Data

US 2014/0148265 A1     May 29, 2014

(51) Int. Cl.
   *A63B 69/36*     (2006.01)
   *A63B 57/00*     (2006.01)
   *A63B 53/06*     (2006.01)

(52) U.S. Cl.
   USPC ............................. 473/199; 473/217; 473/269

(58) Field of Classification Search
   USPC .......................................... 473/199, 217, 269
   IPC ............................................. A43B 3/0005,3/001
   See application file for complete search history.

(56) References Cited

U.S. PATENT DOCUMENTS

| | | | |
|---|---|---|---|
| 5,772,522 A | 6/1998 | Nesbit et al. | |
| 6,567,536 B2 | 5/2003 | McNitt et al. | |
| 2011/0230985 A1* | 9/2011 | Niegowski et al. | 700/91 |

FOREIGN PATENT DOCUMENTS

| | | |
|---|---|---|
| JP | 2006-167397 A | 6/2006 |
| JP | 2011-529352 A | 12/2011 |
| KR | 10-0129095 B1 | 11/1997 |
| KR | 10-2007-0013395 A | 1/2007 |
| KR | 10-0772497 B1 | 11/2007 |
| KR | 10-2010-0089152 A | 8/2010 |
| KR | 10-1135353 B1 | 4/2012 |
| WO | WO-2006/027626 A2 | 3/2006 |
| WO | WO-2006/081395 A2 | 8/2006 |
| WO | WO-2009/060010 A2 | 5/2009 |

* cited by examiner

*Primary Examiner* — William M. Brewster
(74) *Attorney, Agent, or Firm* — NSIP Law

(57) ABSTRACT

A weight shift feedback apparatus senses a weight shift in a golf swing motion of the user, collects, synchronizes and stores the sensed weight shift information, analyzes a weight value applied to each foot of the user with respect to time based on the stored data, and extracts important points of a swing. The weight shift of the user may be evaluated based on an address point, a backswing top point, an impact point, and a point where the weight value applied to each foot has a maximum value, and the feedback information for the evaluation may be provided to the user.

18 Claims, 7 Drawing Sheets

Fig.6A

| RPEAK SECTION | FEEDBACK | SCORE |
|---|---|---|
| ① | When initially performing a back swing from the address, a club is pulled fast by the hand and the weight is shifted fast. Please do not pull the club fast at backswing and swing the club at a slower tempo while pushing the club by the left shoulder. | 50 |
| ② | Great! Weight of the right foot is shifted ideally. | 100 |
| ③ | At the backswing, weight is not sufficiently shifted to the rear foot, and at the downswing, weight is rather applied to the rear foot. This phenomenon occurs when rebounding while pulling a club fast at the backswing top. Please shift the weight to the rear foot more resolutely in the backswing section, and swing the club in the downswing section as if softly moving the weight to the left | 50 |
| ④ | It's a traditional baseball swing form. You may as well perform the weight-shifting exercise for the golf swing from the first. | 20 |

Fig.6B

| LPEAK SECTION | FEEDBACK | SCORE |
|---|---|---|
| BACKSWING TOP | | |
| ① | You shift weight too fast. You are overambitious to hit a ball strongly. Swing speed comes from softness. Please shift weight softer and slower at the initial stage of downswing. You may find a sense of rhythm while exercising swings without a ball. | 30 |
| ② | | 40 |
| ③ | | 50 |
| ④ | The point of shifting the maximum weight to the left foot is too fast. Please swing a club with a feeling of extending the swing longer. You may find a sense of rhythm while exercising swings without a ball. | 60 |
| ⑤ | | 70 |
| ⑥ | | 80 |
| ⑦ | You have good weight shift tendency. Please maintain the present feeling and impact a ball while shifting the weight to the target very slightly. | 90 |
| ⑧ | Great! Weight of the left foot is shifted ideally. | 100 |
| ⑨ | You have good weight shift tendency. Please maintain the present feeling and move your body slower, which has moved toward the target, while pushing the ground slightly faster by the left foot. | 90 |
| ⑩ | The point where the weight is applied most to the left foot is too delayed. Please push the ground by the left foot slightly faster than the present. | 80 |
| IMPACT | | |

FEEDBACK APPARATUS AND METHOD FOR IMPROVING WEIGHT SHIFT

BACKGROUND

1. Field

The present disclosure relates to evaluation of a weight shift in a golf swing, and more particularly, to an apparatus and method for evaluating a weight shift at each foot in the swing motion of a user and providing a graded feedback.

2. Description of the Related Art

Even though the golf has become popular and related industries have been developed, the golf is one of sports whose skills are not easily trained. This is because the golf swing requires a complicated mechanism composed of fixation of the line of vision, center of gravity, movement, swing trajectory or the like, rather than physical conditions.

In the golf swing, it is not easy to figure out points to be improved by exercise, and even though being rectified by a professional coach, it is not easy to link the rectification to actual swing feeling or mechanism. Therefore, there is needed a device which may induce improvement of swing by feeding through automatic analysis and rating of essential swing elements and their visualized information for a correct swing to a user.

In particular, in such an automatic analyzing device for essential elements of a golf swing, the demand and importance of a weight shift, which is a key element for the improvement of a direction and a flying distance of a hit ball, is increasing. In the golf swing, the weight shift represents the change of the weight transferred to both feet or the center of gravity during sequential golf swings including important motions of address, back swing, backswing top, down swing, impact and follow-through.

Generally, in a golf swing, as the central axis of a human body moves, the weight shift, the turning of the human body and the speed of a golf club are associated to hit a ball. Therefore, it is possible to accurately improve a direction and a flying distance of a hit ball only when the weight shifts accurately during the swing. If the weight shift is not performed accurately, a ball may not be hit in a desired direction, and a flying distance decreases. An immoderate swing intended to increase a flying distance may damage joints such as the waist, the neck, the shoulder and the wrist. Therefore, since the accurate weight shift has a very close relation with accurate impact, prevention of a slice, and the increase of a flying distance caused by the improvement of a club head speed, the improvement of a swing posture based on an accurate weight shift is very important.

Nevertheless, conventional golf exercise instruments do not provide a solution for a user to improve a weight shift since they are not able to analyze and diagnose weight shift results and thus not able to provide a suitable feedback.

SUMMARY

The present disclosure is directed to providing a feedback for a swing motion so that a weight shift is performed to a user at a suitable point, by sensing a golf swing motion of the user and analyzing the weight shift.

In one aspect, there is provided a weight shift feedback apparatus, which includes: a sensing unit for sensing a weight shift in a golf swing motion of the user; a data storing unit for collecting, synchronizing and storing the sensed weight shift information; an analyzing unit for analyzing a weight value applied to each foot of the user with respect to time based on the stored data; a time section determining unit for dividing each interval between an address point, a middle-of-back swing point, a backswing top point and an impact point of the swing motion into a plurality of equivalent time sections and determining a time section containing a point where the weight value applied to each foot has a maximum value; and an output unit for providing feedback information to the user based on the determined time section.

In another aspect, there is provided a weight shift feedback method, which includes: sensing a weight shift in a golf swing motion of the user; collecting, synchronizing and storing the sensed weight shift information; analyzing a weight value applied to each foot of the user with respect to time based on the stored data; dividing each interval between an address point, a middle-of-back swing point, a backswing top point and an impact point of the swing motion into a plurality of equivalent time sections; determining a time section containing a point where the weight value applied to each foot has a maximum value, from the plurality of equivalent time sections; and providing feedback information to the user based on the determined time section.

According to an embodiment of the present disclosure, it is possible to provide a graded feedback and a score for improving a weight shift by analyzing weight shift data during a golf swing of a user, and accordingly it is possible for the user to check his weight shift and correct problems by himself.

BRIEF DESCRIPTION OF THE DRAWINGS

The above and other aspects, features and advantages of the disclosed exemplary embodiments will be more apparent from the following detailed description taken in conjunction with the accompanying drawings in which:

FIG. 6a is a relation table showing time section—feedback comment—score at a right foot according to an embodiment of the present disclosure;

FIG. 6b is a relation table showing time section—feedback comment—score at a left foot according to an embodiment of the present disclosure.

DETAILED DESCRIPTION

Hereinafter, embodiments of the present disclosure will be described in detail with reference to the accompanying drawings.

Figure 1:
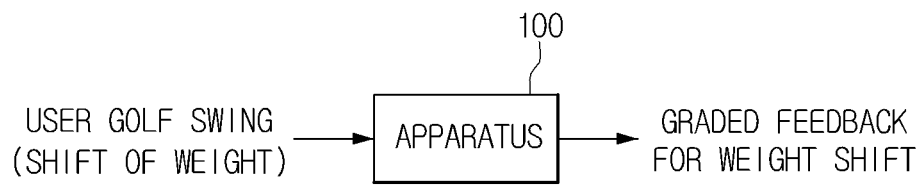
FIG. 1 is a block diagram showing an apparatus for evaluating a weight shift of a user according to an embodiment of the present disclosure.

FIG. 1 shows an apparatus 100 for inputting a weight shift of a user according to a golf swing of a user and providing an evaluation for the weight shift to the user according to an embodiment of the present disclosure.

The weight shift feedback apparatus 100 according to an embodiment of the present disclosure senses, analyzes and evaluates a weight shift at sequential golf swing motions of the user and provides a graded feedback for improving a weight shift in the golf swing of the user.

Figure 2:
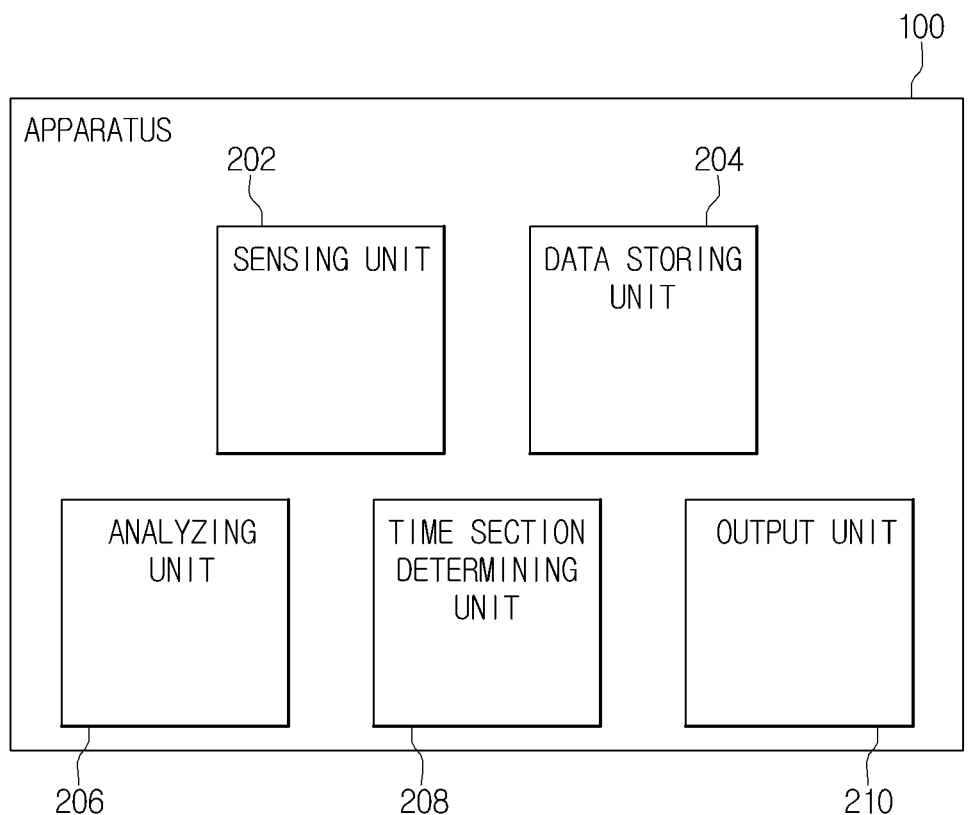
FIG. 2 is a diagram showing a weight shift feedback apparatus according to an embodiment of the present disclosure.

Referring to FIG. 2, the weight shift feedback apparatus 100 according to an embodiment of the present disclosure includes a sensing unit 202 for sensing a weight shift of a user in sequential swing motions, a data storing unit 204 for collecting, synchronizing and storing weight shift information sensed in the sequential swing motions, an analyzing unit 206 for analyzing a weight value applied to each foot of the user with respect to time based on the data collected from the sequential swing motions, a time section determining unit 208 for dividing each interval between an address point, a middle-of-back swing point, a backswing top point, a middle-of-down swing point and an impact point into a plurality of equivalent time sections and determining a time section having a point where the weight value applied to each foot has a maximum value, and an output unit 210 for providing feedback information to the user based on the determined time section.

The sensing unit 202 of the weight shift feedback apparatus according to an embodiment of the present disclosure collects data about a swing posture through a sensor in order to measure the change of a weight shift according to the progress of swing when the user makes a golf swing. In order to calculate the weight shift, data such as the shift of weight and the shift of the center of gravity according to the progress of swing should be measured. For this purpose, various sensors may be utilized.

For example, a ground reaction value of each of both feet may be measured by using a pressure sensor in order to measure the change of a weight shift, or a vision sensor may also be used to detect a user and may monitor the shift of the center of gravity of the user to deduce the change of a weight shift.

The sensing unit according to an embodiment of the present disclosure may have two sensors, each for each foot. By sensing the weight of both feet, the status of a weight shift of the user may be figured out more accurately. The sensor may be a piezoelectric element or may have a string gauge. The piezoelectric element outputs a voltage according to pressure to sense weight by using the output voltage. The string gauge measures the change of tension of a string to sense weight. In addition, any sensor capable of measuring weight may be used without limitation.

In the sensing unit of the apparatus according to an embodiment of the present disclosure, the sensor for sensing a golf swing motion may use either a contact-type sensor or a non-contact type sensor.

In detail, in the contact type, in a state where a sensor is attached to or contacts a human body, location, rotation or movement information of the contacting sensor is received to tract a motion. Representatively, systems using an optical motion tracker (which attaches a marker to a human body to be traced and traces a motion of the marker in a three-dimensional space according to the body motion), an acceleration sensor (which is attached to a human body and outputs an acceleration value of the attachment portion according to a motion to estimate a motion of the body), a pressure sensor (which measures an input pressure, and for example, in a case where pressure sensors are installed at the bottoms of both feet, the pressure sensors may measure the change of ground reaction force according to time), an IMU sensor (which outputs the degree of turn of a body portion to which the sensor is attached) or the like may be used.

In the non-contact type, in a state where a sensor or other substance is not attached or adhered to a human body, a body motion is traced by using a camera (or, a vision sensor). Since a user does not feel sense of difference, the user may perform a free swing. The vision sensor may employ various kinds of sensors such as Charged Coupled Device (CCD) sensor, Pinned Photo Diode (PPD), Charge and Injection Device (CID), Active Pixel Sensor (APS), Active Column Sensor (ACS) or the like.

In detail, in an embodiment of the present disclosure, a method for recognizing a motion of a marker, a marker-less user or a golf club by using a vision sensor, a method for recognizing a motion by using an IMU sensor attached to a human body, a method for deducting a swing posture by using the change of a turning angle calculated from data successively input through IMU sensors attached to the arm and the golf club, or the like may be used for defining important postures of the golf swing.

The data storing unit 204 of the weight shift feedback apparatus according to an embodiment of the present disclosure sequentially receives information for measuring a weight shift in the golf swing of a user input from the sensing unit 202 and collects the information till the termination point of the swing. The termination point of the swing may be determined in various ways, such as by an input of a user or a vision sensor, by recognition of a motion by using a sensor or the like. In addition, in a case where data for measuring the change of a weight shift is collected from a plurality of identical or different sensors, the data may be accurately synchronized and stored on a time axis in the data storing unit 204.

For example, in a case where pressure sensors are used for both feet in order to successively measure a ground reaction value of each of the right and left feet while the user progresses a golf swing, the data sequentially collected from the sensors may be accurately synchronized and stored in the data storing unit 204. In another example, in a case where a pressure sensor or a vision sensor is used to extract important swing points for a swing motion of the user, the data sequentially collected from each sensor may be accurately synchronized and stored in the data storing unit 204.

Figure 3:
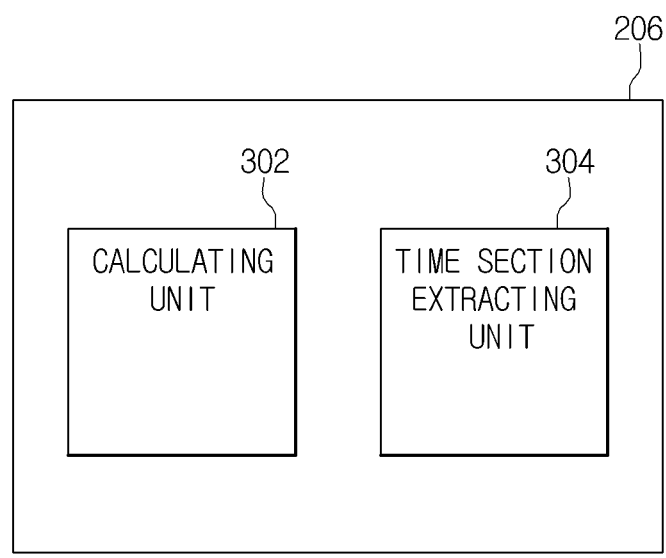
FIG. 3 is a diagram showing an analyzing unit of the weight shift feedback apparatus according to an embodiment of the present disclosure.

Referring to FIG. 3, the analyzing unit 206 of the weight shift feedback apparatus according to an embodiment of the present disclosure may include a calculating unit 302 and a point extracting unit 304.

The analyzing unit 206 of the weight shift feedback apparatus according to an embodiment of the present disclosure may analyze data accumulated till the termination of the swing of the user in order to measure the change of a weight shift in the golf swing of the user. The analyzing unit 206 may receive a group of sequential ground reaction data of each foot collected in the golf swing of the user or certain data sensed by the sensing unit, and express the ground reaction data of each of the right and left feet again on a time axis.

The calculating unit 302, which may be included in the analyzing unit 206 of the weight shift feedback apparatus according to an embodiment of the present disclosure, may calculate the change of a relative angle of the golf club in a swing motion based on the change of a ground reaction value according to time by a swing motion and the location of the golf club at an address posture. In another case, in case of using a certain motion sensor such as a vision sensor, the change of a weight value applied to each foot according to time may be calculated by deduction. In detail, in case of using a vision sensor, the weight applied to a foot may be deducted by observing the shift of the center of gravity when the user makes a swing motion.

The point extracting unit 304, which may be included in the analyzing unit 206 of the weight shift feedback apparatus according to an embodiment of the present disclosure, may extract a point on a time axis with respect to important postures (namely, an address, a middle-of-back swing, a backswing top, a middle-of-down swing and an impact) during a golf swing and a point at a specific value in the change of a weight value (or a ground reaction value) applied to each foot according to time, which are demanded for evaluating a graded weight shift of the user.

The point extracting unit 304 may extract important swing points according to a relative turning angle of the golf club based on the address point in view of the calculation result and also extract a point where the weight value applied to each foot has a maximum value.

The important swing points may include an address point, a backswing top point, an impact point, a middle-of-back swing point and a middle-of-down swing point in order to evaluate a weight shift.

In the golf swing motion according to an embodiment of the present disclosure, when the direction of the golf club is assumed as a reference club direction, the important points may be extracted based on the angular speed.

In a general golf swing, since a back swing starts after a posture is maintained for a certain time at the address posture, before initiating a swing, the reference club direction and a present golf club direction do not change greatly for a certain time. In other words, the angular speed corresponding to the angle between the reference club direction and the present golf club direction will be close to 0. In addition, since the posture is also maintained for a certain time at the backswing top point, the angle between the reference club direction and a present golf club direction will not change greatly for a certain time, which means that the angular speed is close to 0. In the instant of an impact, the angle will decrease and then increase, and the angular speed changes from a negative value to a positive value. Therefore, a zero-crossing point of the angular speed may be defined as the impact point.

In the golf swing motion according to an embodiment of the present disclosure, important points may also be extracted based on a relative turning angle of a golf club. In this case, the angle at the address posture may be used as a reference, and the address posture may be defined as in a direction where the club head is perpendicular to the ground.

In view of the relative turning angle of the golf club, the golf club turning angle will have a maximum value at the backswing top point, decrease again after the backswing top, and then become close to 0 if the golf club returns to the address point again from the impact point.

In an embodiment, important points may be defined in a way that the address point and the backswing top point may be defined based on the angle between the reference club direction and the present club direction, and the impact point may be defined by sensing an instant where a ball starts moving when being actually hit, by using a sensor.

Figure 4:
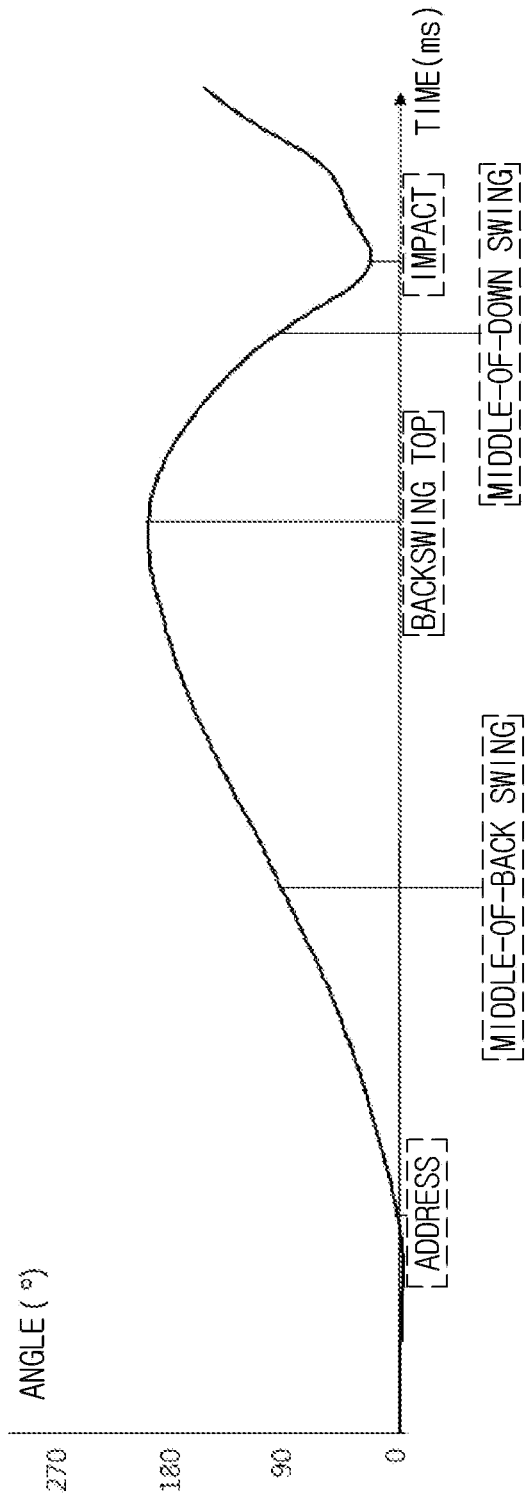
FIG. 4 is a graph showing the change of a turning angle of a golf club and important swing points based on the angle in sequential time-based swings according to an embodiment of the present disclosure.

In addition, the middle-of-back swing point and the middle-of-down swing may be defined as certain intermediate points between the address point and the backswing top point and between the backswing top and the impact point, extracted before, based on statistical analysis of a golf swing specialist group. Generally, the middle-of-back MB swing and the middle-of-down MD swing are defined as follows. The middle-of-back swing is defined as a point where the golf club becomes in parallel with the ground when a back swing is in progress after the address, and the middle-of-down swing is defined as a point where the golf club becomes in parallel with the ground when a down swing is in progress after the backswing top. Based on the above definitions, the instants of both the middle-of-back swing and the middle-of-down swing may be obtained in various ways. FIG. 4 shows important points of a golf swing based on turning data of an IMU sensor mounted to a golf club according to an embodiment of the present disclosure. In detail, X-axis represents time, Y-axis represents an interior angle between the direction of a golf club at the address and a present direction of the golf club, and FIG. 4 shows an address point, a middle-of-back swing point, a backswing top point, a middle-of-down swing point and an impact point. The middle-of-back swing point may be defined as a point where the present golf club direction becomes perpendicular to the direction of the golf club at the address posture when a back swing is in progress after the address, and the middle-of-down swing point may be defined as a point where the present golf club direction becomes perpendicular to the direction of the golf club at the address posture when a down swing is in progress after the backswing top. In other words, based on the direction of the golf club at the address posture, points where an interior angle between the directions of the golf club when a back swing and a down swing are in progress and the reference direction becomes 90 degrees may be defined as the middle-of-back swing and the middle-of-down swing, respectively.

When a golf swing is performed according to an embodiment of the present disclosure, for a correct weight shift, a swing motion should be performed so that a maximum weight is applied to each of the right and left feet at a suitable time point. For example, in a case where important points and a point of a maximum ground reaction value should be extracted and determined based on the change of ground reaction, the sequential motion from the address through the middle-of-back swing, the backswing top and the middle-of-down swing till the impact is divided into certain regions, and then it is determined whether a weight shift is desirably performed based on the region including a point corresponding to the maximum ground reaction.

When a golf swing is performed with a correct weight shift, the ground reactions of the right and left feet change as follows for example. In sequential golf swing motions of a right-handed person from an address through a middle-of-back swing, a backswing top and a middle-of-down swing till an impact, the weight shift may be defined as desirable when a maximum ground reaction of the right foot occurs in a region between the middle-of-back swing and the backswing top, and when a maximum ground reaction of the left foot occurs at the region between the backswing top and the impact.

Figure 5A:
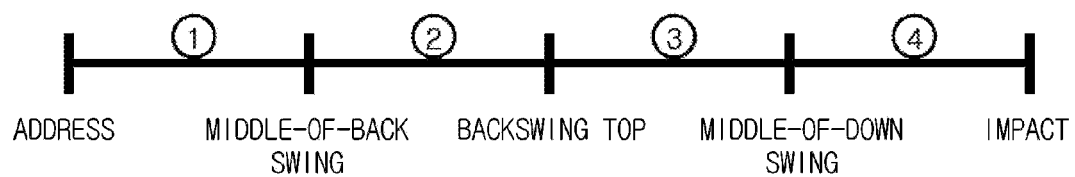
FIG. 5a shows important postures of the swing motion, divided into each time section, according to an embodiment of the present disclosure.
Figure 5B:
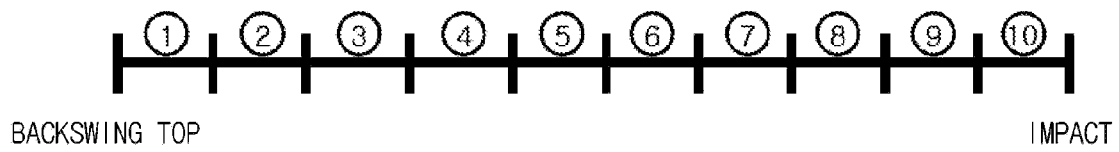
FIG. 5b shows equivalent ten time sections from a backswing top point to an impact point according to an embodiment of the present disclosure.
Figure 7:
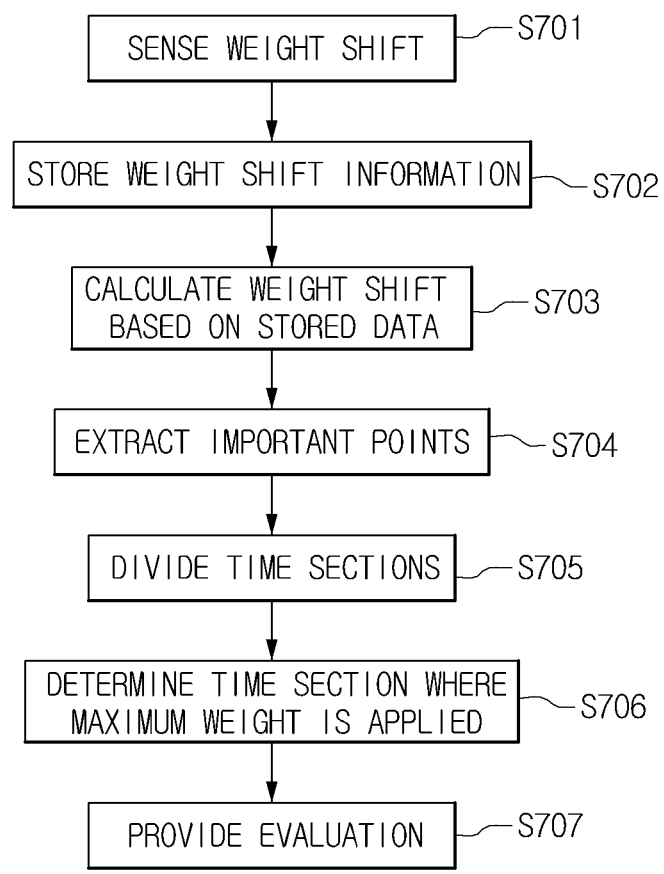
FIG. 7 is a flowchart for illustrating a weight shift feedback method according to an embodiment of the present disclosure.

In detail, FIG. 5a shows that a swing motion is divided based on important points in order to evaluate a weight shift by means of the ground reaction of the right foot. The maximum ground reaction of the right foot occurs at a region between the middle-of-back swing and the backswing top (see the region ② of FIG. 5a). FIG. 5b shows that a swing motion is equivalently divided in order to evaluate a weight shift by means of the ground reaction of the left foot. When the time section from the backswing top to the impact is divided into 10 equivalent sections, the weight shift may be defined as desirable when the maximum ground reaction of the left foot occurs at an $8^{th}$ region from the backswing top point (see ⑧ of FIG. 5b). Even though the above description is based on a right-handed person, the point of the maximum ground reaction of the right and left feet of a left-handed person will be contrary to that of a right-handed person.

The time section determining unit 208 of the weight shift feedback apparatus according to an embodiment of the present disclosure may divide each interval between the address point, the backswing top point and the impact point of the swing motion into a plurality of equivalent time sections, and determine a time section including a point where the weight value applied to each foot has a maximum value. For example, the time section including a point where a maximum weight is applied to the right foot may be divided based on the address, the middle-of-back swing, the backswing top, the middle-of-down swing and the impact point, and the time section including a point where the weight applied to the left foot has a maximum value may be determined by dividing the time section from the backswing top to the impact point into a plurality of equivalent time sections (for example, 10 sections).

The output unit 210 included in the weight shift feedback apparatus according to an embodiment of the present disclosure may provide the evaluation of the time section determining unit 208 as graded feedback information to the user by using a display device or a sound device having a graphic-based interface or a voice-based interface. The feedback information may be a feedback comment or a score. And, the feedback comment or score may be generated in advance according to the degree of weight shift based on the information collected from a golf swing specialist group and stored in the data storing unit 204. For example, the feedback information may be provided based on a relation table associated with time section—feedback comment—score, previously stored in the data storing unit 204.

Referring to FIGS. 6a and 6b, in the output unit 210 of the weight shift feedback apparatus according to an embodiment of the present disclosure, a feedback or score generated based on the divided time section including a point where a maximum ground reaction value of the right and left feet occurs is shown. Four regions shown in FIG. 6a may correspond to four regions of FIG. 5a, and each region of FIG. 6b may correspond to each region of FIG. 5b.

A weight shift feedback method according to an embodiment of the present disclosure may include sensing a weight shift in a swing motion of a user (S701), collecting, synchronizing and storing the weight shift information (S702), analyzing a weight value applied to each foot of the user with respect to time based on the stored data (S703, S704), dividing each interval between an address point, a backswing top point and an impact point of the swing motion into a plurality of equivalent time sections (S705), determining a time section containing a point where the weight value applied to each foot has a maximum value, from the plurality of equivalent time sections (S706), and providing feedback information to the user based on the determined time section (S707).

Operation S701 of sensing a weight shift in a swing motion of a user according to an embodiment of the present disclosure may be performed by measuring a ground reaction of each of both feet by using a pressure sensor or the like, or the weight shift may also be measured by observing the shift of the center of gravity of the user after detecting a swing motion of the user by using a vision sensor, IMU sensor or the like.

Operations S703, S704 of analyzing a weight value applied to each foot of the user with respect to time according to an embodiment of the present disclosure may include calculating the change of a relative angle of a golf club in the swing motion based on the change of a weight shift and a location of the golf club at an address posture (S703), and extracting important points (an address, a middle-of-back swing, a backswing top, a middle-of-down swing, and an impact point) of the golf swing and a point where the weight value applied to each foot has a maximum value (S704). In Operation S703 of calculating the change of a weight shift or a relative angle of a golf club, a ground reaction value varying according to time may be calculated, or in a case where a vision sensor is used, the weight value applied to each foot may be deducted to calculate the change according to time.

In Operation S707 of providing feedback information with respect to the time section containing a point where the weight value applied to each foot has a maximum value, the right and left feet may be evaluated respectively. In detail, a right foot may be evaluated based on five time sections including an address, a middle-of-back swing, a backswing top, a middle-of-down swing and an impact point, as important postures (points) of the golf swing. In addition, the weight shift may be evaluated as being most desirable when the point where the ground reaction of the right foot has a maximum value occurs at the time section between the middle-of-back swing and the backswing top, and provided as the feedback information. The feedback information may be a feedback comment or a score without being limited thereto.

According to an embodiment of the present disclosure, Operation S707 of providing the evaluation result to the user as feedback information by using a display device or a sound device may be performed. Referring to FIGS. 6a and 6b, a graded feedback and a score are displayed with respect to the weight shift of the user, and the apparatus according to an embodiment of the present disclosure may provide a graded feedback to the user based on the data provided from a specialist group.

The above methods may be implemented with various computer-executable programs and recorded on computer-readable media. The computer-readable media may include program commands, data files, data structures or the like, solely or in combination.

Even though the present disclosure has been described with reference to the embodiments depicted in the drawings, it is just an example, and a person skilled in the art will understand that various changes or modifications can be made therefrom. However, such modifications should be regarded as belonging to the scope of the present disclosure. Therefore, the sincere scope of the present disclosure should be defined by the appended claims.

What is claimed is:

1. A weight shift feedback apparatus comprising:
a sensing unit configured to sense a weight shift applied to each foot of a user in a golf swing motion of the user;
an analyzing unit configured to analyze a weight value applied to each foot of the user with respect to time;
a time section determining unit configured to divide each interval between an address point, a middle-of-back swing point, a backswing top point and an impact point of the swing motion into a plurality of equivalent time sections and to determine, for each foot, a time section containing a point where the weight value applied to the foot has the maximum value; and
an output unit configured to provide feedback information to the user based on the determined time sections, wherein
the time section determining unit determines whether a point where the maximum weight value applied to the right foot is between the middle-of-backswing point and the backswing top point and whether a point where the maximum weight value applied to the left foot is between the backswing top point and the impact point.

2. The weight shift feedback apparatus according to claim 1, wherein the sensing unit includes a pressure sensor configured to measure a ground reaction value of each foot of the user.

3. The weight shift feedback apparatus according to claim 1, wherein the sensing unit includes a vision sensor for sensing a weight shift of the user by detecting a swing motion of the user and observing a shift of the center of gravity of the user.

4. The weight shift feedback apparatus according to claim 2, wherein the analyzing unit includes:
   a calculating unit configured to calculate the change of a relative angle of a golf club in the swing motion based on a change of the ground reaction value according to time and a location of the golf club at an address posture; and
   a point extracting unit configured to extract the point where the weight value applied to each foot has the maximum value, from the address point, the middle-of-back swing point, the backswing top point and the impact point, based on the calculation result.

5. The weight shift feedback apparatus according to claim 1, wherein:
   the output unit provides the user with the feedback information about whether a maximum ground reaction of the left foot occurs at an $8^{th}$ time section from the backswing top point, when the time section from the backswing top point to the impact point is divided into equivalent ten sections, and whether a maximum ground reaction of the right foot occurs at a time section between the middle-of-back swing point and the backswing top point,
   when the back swing is in progress after the address, the middle-of-back swing point is defined as a point where a direction of the golf club is perpendicular to the direction of the golf club at an address posture, and
   the feedback information is provided to the user based on a relation table relating to a feedback comment and score for each time section previously stored.

6. The weight shift feedback apparatus according to claim 1, further comprising:
   a data storing unit configured to collect, synchronize, and store the sensed weight shift information, wherein
   the analyzing unit analyses a weight value applied to each foot of the user based on the stored data with respect to time.

7. The weight shift feedback apparatus according to claim 1, wherein the output unit provides the feedback information to the user by using a display device or sound device having a graphic-based interface or a voice-based interface.

8. A weight shift feedback method comprising:
   sensing a weight shift applied to each foot of a user in a golf swing motion of the user;
   analyzing a weight value applied to each foot of the user with respect to time;
   dividing each interval between an address point, a middle-of-back swing point, a backswing top point and an impact point of the swing motion into a plurality of equivalent time sections;
   determining, for each foot, a time section containing a point where the weight value applied to the foot has the maximum value, from the plurality of equivalent time sections; and
   providing feedback information to the user based on the determined time sections, wherein
   said determining the time section containing the point where the weight value applied to each foot has the maximum value comprises determining whether a point where the maximum weight value applied to the right foot is between the middle-of-backswing point and the backswing top point and whether a point where the maximum weight value applied to the left foot is between the backswing top point and the impact point.

9. The weight shift feedback method according to claim 8, wherein said sensing of a weight shift applied to each foot of a user in a golf swing motion of the user includes measuring a ground reaction value of each foot of the user.

10. The weight shift feedback method according to claim 8, wherein said sensing of a weight shift applied to each foot of a user in a golf swing motion of the user includes sensing a weight shift applied to each foot by detecting a swing motion of the user and then observing a shift of the center of gravity of the user.

11. The weight shift feedback method according to claim 9, wherein said analyzing of a weight value applied to each foot of the user with respect to time includes:
   calculating a change of a relative angle of a golf club in the swing motion based on a change of the ground reaction value according to time and a location of the golf club at an address posture; and
   extracting a point where the weight value applied to each foot has the maximum value, from the address point, the middle-of-back swing point, the backswing top point and the impact point, based on the calculation result.

12. The weight shift feedback method according to claim 10, wherein said analyzing of a weight value applied to each foot of the user with respect to time includes:
   calculating a change of the weight value applied to each foot of the user with respect to time based on the sensed weight shift;
   extracting the address point, the middle-of-back swing point, the backswing top point, and the impact point according to a change of a relative angle of a golf club in the swing motion based on the location of the golf club at the address posture; and
   extracting a point where the weight value applied to each foot has the maximum value, based on the calculation result.

13. The weight shift feedback method according to claim 8, wherein said providing of feedback information to the user includes:
   providing the user with feedback information about whether a maximum ground reaction of the left foot occurs at an $8^{th}$ time section from the backswing top point, when the time section from the backswing top point to the impact point is divided into equivalent ten sections, wherein
   the feedback information is provided based on a relation table relating to a feedback comment and score for each time section previously stored.

14. The weight shift feedback method according to claim 8, wherein said providing of feedback information to the user includes:
   providing the user with a feedback comment on whether a maximum ground reaction of the right foot occurs at a time section between the middle-of-back swing point and the backswing top point, wherein:
   the middle-of-back swing point is defined as a point where the direction of the golf club, when the back swing is performed after the address, becomes perpendicular to the direction of the golf club at an address posture, and
   the feedback comment is provided based on a relation table relating to a feedback comment and score for each time section previously stored.

15. The weight shift feedback method according to claim 8, wherein said providing of feedback information to the user includes:
- providing the user with the feedback information about whether a maximum ground reaction of the left foot occurs at an $8^{th}$ time section from the backswing top point, when the time section from the backswing top point to the impact point is divided into equivalent ten sections; and
- providing the user with a feedback comment on whether a maximum ground reaction of the right foot occurs at a time section between the middle-of-back swing point and the backswing top point, wherein:
- the middle-of-back swing point is defined as a point where the direction of the golf club, when the back swing is performed after the address, becomes perpendicular to the direction of the golf club at an address posture, and
- the feedback comment is provided based on a relation table relating to a feedback comment and score for each time section previously stored.

16. The weight shift feedback method according to claim 12, wherein, in said extracting of the address point, the middle-of-back swing point, the backswing top point, and the impact point according to a change of a relative angle of a golf club in the swing motion based on the location of the golf club at the address posture, a relative angular speed of the golf club is 0 at the address point and the backswing top point, and the impact point is a point where a relative angular speed of the golf club changes from a negative value to a positive value.

17. The weight shift feedback method according to claim 8, further comprising:
- collecting, synchronizing and storing the sensed weight shift information, wherein
- in said analyzing of a weight value applied to each foot of the user with respect to time, the weight value is analyzed with respect to time based on the stored data.

18. The weight shift feedback method according to claim 8, wherein said providing of feedback information to the user includes providing the feedback information to the user by using a display device or a sound device having a graphic-based interface or a voice-based interface.

* * * * *